(12) United States Patent
Hallman, Jr. et al.

(10) Patent No.: US 8,171,775 B2
(45) Date of Patent: May 8, 2012

(54) MATERIAL PERMEANCE MEASUREMENT SYSTEM AND METHOD

(75) Inventors: Russell Louis Hallman, Jr., Knoxville, TN (US); Michael John Renner, Oak Ridge, TN (US)

(73) Assignee: Babcock & Wilcox Technical Services Y-12, LLC, Oak Ridge, TN (US)

( * ) Notice: Subject to any disclaimer, the term of this patent is extended or adjusted under 35 U.S.C. 154(b) by 1319 days.

(21) Appl. No.: 11/829,602

(22) Filed: Jul. 27, 2007

(65) Prior Publication Data

US 2012/0085150 A1 Apr. 12, 2012

Related U.S. Application Data

(62) Division of application No. 11/240,294, filed on Sep. 30, 2005, now Pat. No. 7,325,439.

(51) Int. Cl.
*G01M 3/02* (2006.01)
(52) U.S. Cl. .......................... 73/37; 73/19.01; 261/64.3
(58) Field of Classification Search .......... 73/37, 19.01, 73/19.02, 19.04, 19.05; 261/43, 64.3, 130
See application file for complete search history.

(56) References Cited

U.S. PATENT DOCUMENTS

| | | | | |
|---|---|---|---|---|
| 3,438,241 A * | 4/1969 | McKinley, Jr. | | 73/31.07 |
| 3,521,865 A * | 7/1970 | Kertzman | | 261/95 |
| 3,917,453 A * | 11/1975 | Milligan et al. | | 435/15 |
| 4,257,257 A * | 3/1981 | Dairaku et al. | | 73/19.02 |
| 4,468,948 A * | 9/1984 | Nakayama | | 73/19.1 |
| 4,715,217 A * | 12/1987 | Coyne et al. | | 73/61.55 |
| 6,182,951 B1 * | 2/2001 | Hallman et al. | | 261/130 |
| 6,439,036 B1 * | 8/2002 | Mansky | | 73/61.41 |
| 6,455,007 B1 * | 9/2002 | Mansky et al. | | 422/553 |
| 6,662,635 B2 * | 12/2003 | Mansky | | 73/61.41 |

* cited by examiner

*Primary Examiner* — Hezron E Williams
*Assistant Examiner* — Samir M Shah
(74) *Attorney, Agent, or Firm* — Michael J. Renner, Esq.; Luedeka Neely Group, P.C.

(57) ABSTRACT

A system for measuring the permeance of a material. The permeability of the material may also be derived. The system provides a liquid or high concentration fluid bath on one side of a material test sample, and a gas flow across the opposing side of the material test sample. The mass flow rate of permeated fluid as a fraction of the combined mass flow rate of gas and permeated fluid is used to calculate the permeance of the material. The material test sample may be a sheet, a tube, or a solid shape. Operational test conditions may be varied, including concentration of the fluid, temperature of the fluid, strain profile of the material test sample, and differential pressure across the material test sample.

4 Claims, 6 Drawing Sheets

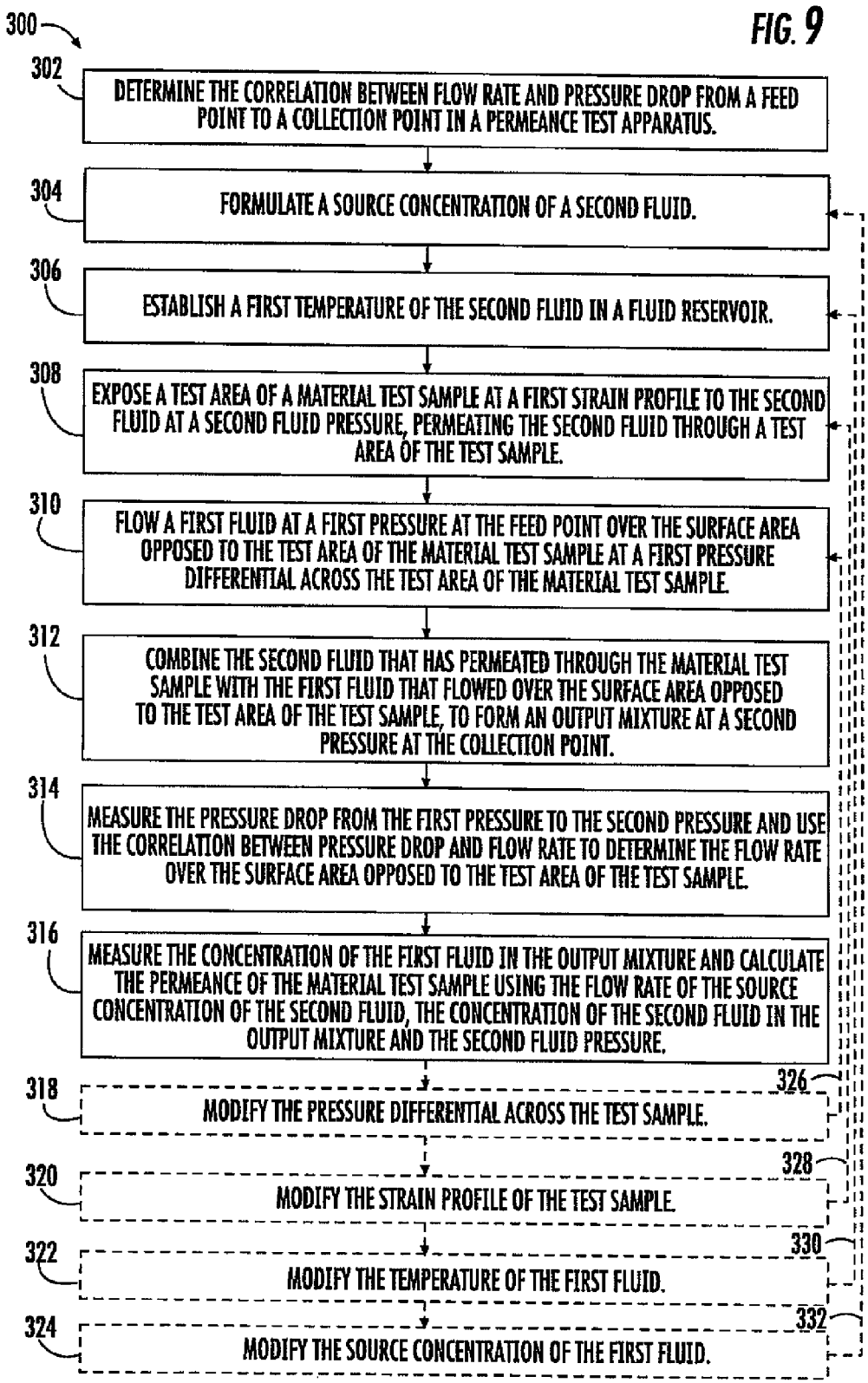

MATERIAL PERMEANCE MEASUREMENT SYSTEM AND METHOD

CROSS REFERENCES TO RELATED APPLICATIONS

This application claims priority from and is a Divisional Application of U.S. patent application Ser. No. 11/240,294 filed Sep. 30, 2005 now U.S. Pat. No. 7,325,439, entitled: Fluid Permeability Measurement System and Method. Patent application Ser. No. 11/240,294 is incorporated by reference in its entirety herein.

GOVERNMENT RIGHTS

The U.S. Government has rights to this invention pursuant to contract number DE-AC05-00OR22800 between the U.S. Department of Energy and BWXT Y-12, L.L.C.

FIELD

This invention relates to the field of material measurement systems. More particularly, this invention relates to the measurement of permeance of materials to liquids, gases, and vapors.

BACKGROUND

Many industrial and consumer products rely on the liquid and vapor permeation property of materials to attain desired effects. For example, residential and commercial construction techniques typically include the installation of a vapor bather to prevent loss of insulative properties of thermal insulation materials. Mechanical and electronic components are often coated with conformal polymeric materials to prevent corrosion. Food products such as cereals and snack products are typically packaged in materials designed to prevent infusion of humidity which reduces crispness. In these applications materials are designed and used to substantially prevent the permeation of fluids in and/or out. However, there are many other industrial and consumer applications that benefit from allowing some permeation of vapors through a material. For example, industrial polymeric membranes are designed to permit the transfer of permeates through their surface. Fabrics for personal outerwear are often treated with polymers for rain resistance, but the removal through the fabric of water vapor generated by the wearer is beneficial to enhance comfort. Contact lenses are designed for gas permeability.

The above examples illustrate the benefit of controlling the permeation of water and other fluids through material surfaces within a range of values. Achieving that objective requires the accurate measurement of permeation rates of vapors through the materials. The ASTM E96-00, "Standard Test Methods for Water Vapor Transmission of Materials," is a standard test method for measuring the water vapor permeability of materials. It is used primarily for construction materials and fabrics to measure the effect that water has on a particular material or product. The desiccant (or "dry cup method") and the water (or "wet cup method") are the two basic methods used for ASTM E96 tests. A variation of the test uses a combination of the two methods where a test compartment is divided into two chambers separated by the material being tested and a moist atmosphere is established in one chamber and a dry atmosphere is in the other. A test is run to determine how much moisture passes through the test material from the "wet" chamber to the "dry" chamber.

Water Vapor Transport is calculated using the formula presented as Equation 1:

$$WVT = (G/t)/A \quad [\text{Eq'n 1}]$$

where G is the weight gain of the desiccant, t is time (typically twenty four hours under ASTM E96), and A is surface area of the material between the chambers. Typically the quantity of G/t is found by plotting the water weight gain or loss versus time and obtaining the slope of that line.

Permeance is calculated from the formula presented as Equation 2:

$$\text{Permeance} = WVT/(S^*(R_1-R_2)) = WVT/\Delta P = G/(t^*A^*\Delta P) \quad [\text{Eq'n 2}]$$

where S is the saturation vapor pressure at test temperature, $R_1$ is the relative humidity at the vapor source, and $R_2$ is the relative humidity at the vapor sink (such as at a desiccant), and $\Delta P$ is the vapor pressure differential. Saturation vapor pressure is the pressure that water vapor creates when the air is fully saturated. When air is at saturation vapor pressure, it is said to be at the dew point. In the dry cup method, the relative humidity inside the test cup is controlled to be approximately 0% and the relative humidity outside of the test cup is generally controlled at a high value, typically 95%-100%. In the wet cup method, the relative humidity inside the test cup is set at a high value, typically 95%-100%, and the humidity outside the cup is controlled to be approximately 0%.

ASTM E96 water vapor transmission measurements are often difficult to make. Sometimes the results obtained by the dry cup method do not agree with results obtained by the wet cup method. These discrepancies are generally attributed to the dominance of factors related to vapor outflow from the test specimen in the dry cup method and dominance of factors related to vapor flow into the test specimen in the wet cup method. Another difficulty is that these tests are typically limited to materials of a particular form such as sheets or films. What is needed, therefore, are mechanisms and methods for more directly and accurately measuring the permeation rate of polymeric and other materials in various forms, including sheets, tubes, and other structures.

SUMMARY

One embodiment of the present invention provides a system for measuring permeance parameters of a tubular material. The system includes a tube having a first end and a second end. The tube also has a hollow passageway with a calibrated resistance, and a permeable section with an outer surface. A first fluid source is configured to feed a first fluid at a first pressure into the hollow passageway at the first end of the tube. There is a second fluid reservoir configured to surround at least a portion of the outer surface of the permeable section of the tube and to infuse a quantity of the second fluid by permeation into the hollow passageway of the tube and thereby form in the hollow passageway a mixture of the second fluid and the first fluid at a concentration level. A pressure gauge in pressure communication with the hollow passageway is provided at the second end of the tube. The pressure gauge is configured to measure a second pressure of the mixture of the first fluid and the second fluid at the second end of the tube. A concentration meter in fluid communication with the hollow passageway at the second end of the tube is provided. The concentration meter is configured to measure the concentration level of the second fluid in the mixture.

An alternative embodiment provides a system for measuring permeance parameters of a material. This embodiment includes a material test sheet having a first surface and an opposing second surface. There is a second fluid reservoir containing a second fluid and a collection chamber having a first fluid source line. A first fluid source is provided for continuously flowing a first fluid at a first pressure into the collection chamber through the first fluid source line. The system further includes a fixture for disposing the material test sheet between the second fluid reservoir and the collection chamber wherein (a) a test area of the first surface of the material test sheet is exposed to the second fluid and (b) the area on the second surface of the material test sheet that opposes the test area of the first surface is exposed to the first fluid in the collection chamber, whereby a portion of the second fluid permeates through the test area into the collection chamber to form in the collection chamber an output mixture of the second fluid and the first fluid at a concentration level. A collection removal line is provided for removing substantially all of the output mixture. There is a pressure gauge in pressure communication with the collection removal line, for measuring a second pressure of the output mixture in the collection removal line, and a concentration meter configured to measure the concentration level of the second fluid in the output mixture exiting from the collection chamber through the collection removal line.

The invention also provides a method for measuring the permeance of a material. The method begins by determining the correlation between flow rate and a pressure drop from a feed point to a collection point in a permeance test apparatus. The next step is exposing a test area of a test sample having a strain profile to a second fluid at a second fluid pressure and a second fluid source concentration for a period of time sufficient to establish a steady state rate of permeation of the second fluid through the test sample. The method continues with flowing a first fluid at a first pressure at the feed point over the surface area opposed to the test area of the test sample at a pressure differential across the test area of the material test sample. Next is the step of combining the second fluid that has permeated through the test sample with the first fluid that flowed over the surface area opposed to the test area of the test sample to form an output mixture. The method then involves measuring the pressure drop from the first pressure to the second pressure and using the correlation between pressure drop and flow rate to determine the flow rate over the surface area opposed to the test area of the test sample of the second fluid in the output mixture. The method concludes with measuring the output concentration of the second fluid in the output mixture and calculating the permeance of the material test sample using the flow rate, the source concentration of the second fluid, the flow rate, the output concentration of the second fluid in the output mixture, and the second fluid source pressure.

The invention also includes an embodiment that provides a system for measuring permeance parameters of a tubular material. The system includes a tube having a first end and a second end and having a hollow passageway. The tube includes a permeable section with an outer surface. There is a first fluid source configured to feed the first fluid at a first pressure into the hollow passageway at the first end of the tube. There is a second fluid reservoir configured to surround at least a portion of the outer surface of the permeable section of the tube and to infuse a quantity of the second fluid by permeation into the hollow passageway of the tube and form in the hollow passageway a mixture of the second fluid and the first fluid at a concentration level. A flowmeter in fluid communication with the hollow passageway at the second end of the tube is provided. The flowmeter is configured to measure the flow rate of the first fluid and the second fluid through the hollow passageway. A concentration meter in fluid communication with the hollow passageway at the second end of the tube is provided. The concentration meter is configured to measure the concentration level of the second fluid in the mixture.

An alternative embodiment provides a system for measuring permeance parameters of a material. The system includes a material test sheet having a first surface and an opposing second surface. There is a second fluid reservoir containing a second fluid and a collection chamber having a first fluid source line. A first fluid source is provided for continuously flowing a first fluid at a first pressure into the collection chamber through a first fluid source line. A fixture is included for disposing the material test sheet between the second fluid reservoir and the collection chamber wherein (a) a test area of the first surface of the material test sheet is exposed to the second fluid and (b) the area on the second surface of the material test sheet that opposes the test area of the first surface is exposed to the first fluid in the collection chamber, whereby a portion of the second fluid permeates through the test area into the collection chamber to form in the collection chamber an output mixture of the second fluid and the first fluid at a concentration level. There is a collection removal line for removing substantially all of the output mixture. A flowmeter in fluid communication with the collection removal line is provided. The flowmeter is configured to measure the flow rate of the first fluid and the second fluid through the collection removal line. There is also a concentration meter that is configured to measure the concentration level of the second fluid in the output mixture exiting from the collection chamber through the collection removal line.

The invention provides a number of advantages for permeation testing. For example, various embodiments provide for easy incorporation of different material test samples. This feature is of particular benefit for material production run testing. In addition, the preferred embodiments provide easy and accurate modification of test conditions which is beneficial for laboratory environments. Also, embodiments are provided to test for permeation of gases and liquids through materials, whereas most commercially available test apparatuses only test for permeation of vapors through materials.

BRIEF DESCRIPTION OF THE DRAWINGS

Further advantages of the invention are apparent by reference to the detailed description in conjunction with the figures, wherein elements are not to scale so as to more clearly show the details, wherein like reference numbers indicate like elements throughout the several views, and wherein:

FIG. 9 is flow diagram of a method according to the invention.

DETAILED DESCRIPTION

Figure 1:
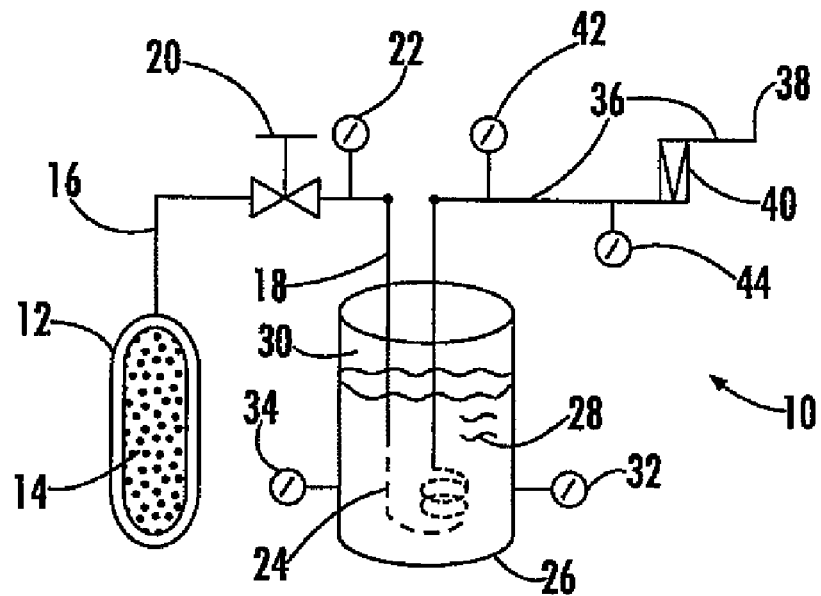
FIG. 1 is a somewhat schematic view of a permeance test apparatus according to the invention.

Materials permit the passage of fluids through their bulk masses, although the extent of such passage varies widely among materials and fluids. Fluids are characterized as liquids, gases, or vapors. A vapor is a gaseous mixture of (1) a material that is commonly solid or liquid at room temperature and (2) a gas. For example, the portion of liquid water in air is commonly referred to as water vapor. In discussing the passage of a fluid through a material, the words permeability, permeance, and permeate are often used. To understand the meaning of these terms it is helpful to refer to the specific case of water vapor passing through a sheet of material. The moisture transmission rate through a material (such as styrene) is referred to as its "permeability." Permeability is a physical property of the material itself, and is not dependent upon the material's thickness. Permeability is difficult to measure directly. Instead, the "permeance" of a sample of the material of known thickness is typically measured, and then permeability is calculated by multiplying the measured permeance by the thickness of the test sample. Permeance is the number that is generally used to compare various materials in regard to moisture (water vapor) transmission resistance, and it is measured in a unit call a "perm." Permeability is measured in "perm-inches" or "perm-centimeters."

For water vapor, in metric (SI) units, a perm is equal to the transfer of $5.7 \times 10^{-11}$ kilograms of water per square meter of material per second under a water vapor pressure difference of 1 pascal. In English units, a perm is equal to the transfer of 1 grain (0.002285 oz.) of water per square foot of material per hour under a water vapor pressure difference of 1 inch of mercury. It is important to note that ASTM E96 permits any one of five combinations of temperature and humidity on the "wet" side of the test chamber. Therefore, permeance results reported without reference to the actual temperature/humidity test conditions are largely meaningless.

The word "permeate" is commonly used as a verb meaning to diffuse through or penetrate something. In technical contexts, especially those related to semi-permeable membranes, the word "permeate" is also used as a noun, referring to the substance that diffuses through a material. In this context the noun "permeate" is typically juxtaposed with the noun "concentrate," where the "permeate" is the portion of the feed material that has passed through the membrane, and the "concentrate" is the portion of the feed which has been rejected by the membrane. Herein the word permeate will be used both as a verb and a noun; it should be evident by the context whether the word "permeate" is being used as a verb or as a noun.

When a material that is permeable to a specific permeate is exposed to a source concentration of the permeate on one side of the material that is different from the output concentration of the permeate on the other side of the material, the permeate will transfer through the material from the higher concentration side to the lower concentration side. The permeability of a specific sample of material depends primarily upon the permeance of the material to a specific permeate, the concentration difference across the two opposing surfaces of the material, the partial pressure gradient for gases and vapors or concentration difference for liquid across the material, and the temperature of the permeate on the concentrate side. Typically, systems are evaluated at thermal equilibrium, so there is no temperature difference from one side to the other. Both sides and the membrane are maintained at one temperature and thus controlled uniformly. Depending on these concentration, pressure, and temperature factors, it may take from a few seconds to many months to reach a steady state flow rate of permeate through the material.

It is often desirable to measure the permeance of such materials as paper, polymers and plastics, acrylics, fiberboards, gypsum and plaster products, and various wood products. Often it is desirable to measure permeance as a function of such environmentally independent variables as temperature, pressure, material strain, and vapor concentration. "Material strain" is the amount of stretch of a material (typically expressed as a percentage elongation compared to the unstretched dimension) induced by a force exerted on the material. The force may be generated by a fluid pressure, a physical deformation, a thermal deformation, or similar force. In order to measure permeance as a function of environmentally independent variables it is necessary to be able to hold all of the independent variables constant except for one variable of interest. Various enablements directed toward that object are best described in reference to the figures.

FIG. 1 illustrates a test apparatus 10 for demonstrating the relationship between pressure differentials and flow rates through tubular materials. A first fluid tank 12 supplies a first fluid 14 under pressure through a supply line 16 to a tube 18. First fluid 14 is typically a gas, such as dry nitrogen, but it may be a vapor or a liquid. A supply valve 20 is used to control the supply pressure of first fluid 14 through supply line 16 and a supply pressure gauge 22 is provided to measure the supply gas pressure. Tube 18 has permeable section 24. A second fluid reservoir 26 containing a second fluid 28 is provided. Second fluid 28 is typically a liquid such as water, but it may be a gas or a vapor. If second fluid 28 is a liquid, second fluid reservoir 26 is generally unpressurized (i.e., the head space 30 is open to the atmosphere. If second fluid 28 is a gas or a vapor, second fluid reservoir 26 is typically closed to the atmosphere and there is no headspace 30. At least a portion of the permeable section 24 of tube 18 is immersed in second fluid 28. It is important for subsequent calculations to know what quantitative length (e.g., "6.0 cm" or "8.5 cm") of the permeable section 24 of tube 18 is immersed in second fluid 28. The quantitative amount of the permeable section 24 of tube 18 that is immersed in second fluid 28, and (as illustrated in FIG. 1) it may be the entire permeable section 24, is referred to as the "immersed portion" of the permeable section 24. A second fluid pressure gauge 32 is generally provided to measure the pressure of second fluid 28 at the elevation of the permeable section 24 of tube 18. A temperature gauge 34 may be provided to measure the temperature of second fluid 28.

First fluid 14 that is supplied to tube 18 flows from tube 18 into discharge line 36 from which it is discharged at discharge line end 38 into the atmosphere, or a suitable trap. A rotameter 40 is positioned in discharge line 36 to measure the volumetric flow rate of first fluid 14 through the system. A discharge pressure gauge 42 is provided to measure the pressure of first fluid 14 as it exits tube 18. If first fluid 14 is discharged into the atmosphere at discharge line end 38, the discharge pressure is atmospheric pressure plus any pressure drop in discharge line 36 between discharge pressure gauge 42 and discharge line end 38. A temperature gauge 44 may be provided to measure the temperature of the first fluid 14 that is discharged from the system. By knowing the composition of first fluid 14, the volumetric flow rate and discharge pressure, the standard volumetric flow rate may be calculated.

Figure 2:
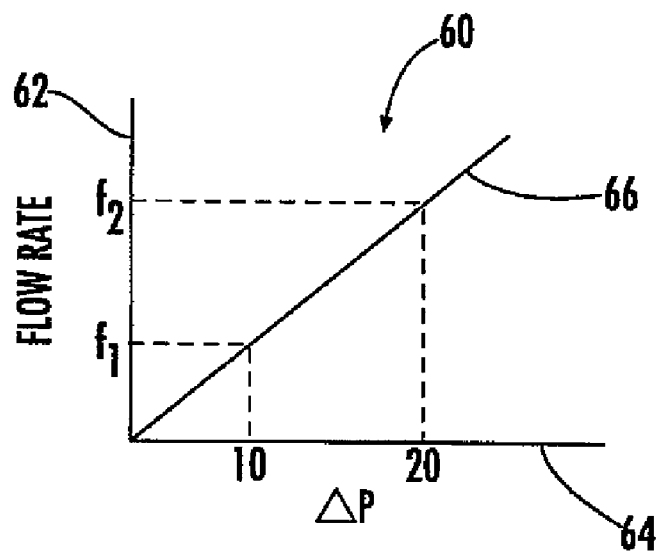
FIG. 2 is a graph showing the relationship between volumetric flow rate and pressure drop across a first fluid carrier in a permeance test apparatus, according to the invention.

FIG. 2 illustrates that typically the relationship between the pressure drop across a tube and the flow rate through a tube is substantially linear, assuming the flow is laminar. If the flow is turbulent, the relationship between pressure drop across the tube and flow rate through the tube is exponential. Graph 60 illustrates that a flow rate (plotted on the ordinate 62) that is linearly proportional to the pressure differential ΔP across a tube (plotted on the abscissa 64) as depicted by curve 66. For example if the pressure differential across a tube is 10 (arbitrary units), and the flow rate is $f_1$ in standard cubic units per time, then when the pressure differential doubles to 20 (arbitrary units) the flow rate is $f_2$ in standard cubic units per time, which is twice $f_1$. Thus, once the resistance of a tube such as tube 18 in FIG. 1 is calibrated with a curve such as illustrated in FIG. 2, rotameter 40 is no longer required because the flow rate through the tube 18 may be determined by measuring the pressure drop (ΔP) across the tube 18 using supply pressure gauge 22 and discharge pressure gauge 42, and reading the flow rate from curve 66 of FIG. 2. Note that the calibrated resistance depicted by curve 66 of FIG. 2 is specific for a specific tube (e.g., tube 18 of FIG. 1). A specific curve 66 must be constructed for each specific tube geometry. The curve 66 will be different for tubes of identical material having either different lengths or different diameters or different interior surface characteristics.

Note that several conditions regarding permeable portion 24 are important for curve 66 to be accurate. First, the permeable portion 24 must not be significantly porous to first fluid 14. That is, substantially all of the first fluid 14 flowing into tube 18 from supply line 16 must exit tube 18 through discharge line 36. Second, permeable portion 24 should preferably be only "semi-permeable" to second fluid 28. That is, second fluid 28 should pass through permeable portion 24 as a vapor or a gas, not as a liquid. Also, curve 66 is typically constructed using only first fluid 14 flowing through tube 18. A large quantity of second fluid 28 entering the permeable portion 24 of tube 18 may reduce the accuracy of curve 66. Generally this is not critical to measurements because the percentage of second fluid 28 that permeates the permeable section 24 is on the order of less than parts-per-thousand, which does not significantly affect the accuracy of flow rates determined by curve 60 for most purposes. For high permeation rates calibration curves may be developed accounting for both fluid 14 and 28.

Figure 3:
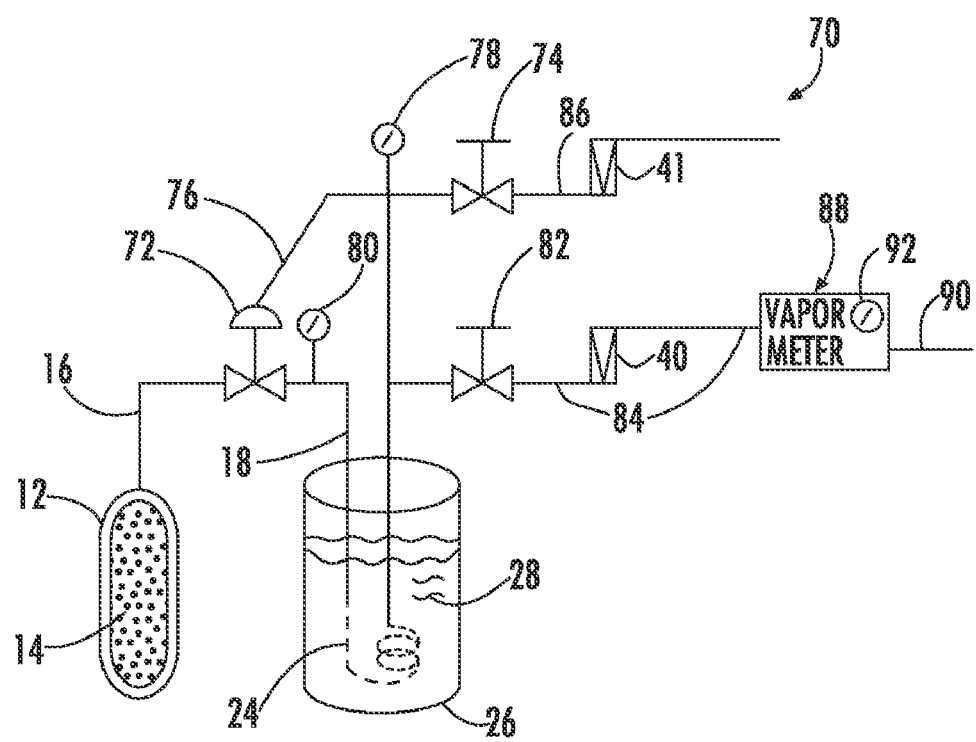
FIG. 3 is a somewhat schematic view of an alternative permeance test apparatus, according to the invention.

In some applications it may be beneficial to automatically control the pressure drop across tube 18. Such automatic control is particularly useful if the pressure at line end 38 varies erratically, or if the pressure of first fluid 14 in first fluid supply tank 12 is not stable. FIG. 3 illustrates an embodiment, permeance test apparatus 70, that provides automatic pressure control. FIG. 3 also illustrates other features that may be included in a permeance measurement system. For example, supply valve 20 of FIG. 1 has been replaced with differential supply regulator 72 in FIG. 3. Differential supply regulator 72 works in cooperation with back pressure control valve 74 through pilot tube 76 to maintain a constant pressure drop across tube 18 in permeance test apparatus 70, as measured by output pressure gauge 78 and input pressure gauge 80.

To calibrate the flow resistance of tube 18, second fluid reservoir 26 is typically purged of any second fluid 28, the back pressure control valve 74 is set at atmospheric pressure, the differential supply regulator 72 is set at the desired minimum differential pressure (e.g., ~0) and the flow rate is read from a rotameter 41 attached to line 86. The differential supply pressure is increased by adjustment of the differential supply regulator 72 and the new flow rate at the new pressure is read. The pressure delivered by the differential supply regulator 72 is again increased to the desired pressure range and the flow rate read. The process is repeated until the desired differential pressure range has been spanned for the current back pressure regulator 74 setting. The back pressure maintained by the back pressure regulator 74 is then increased and the differential supply regulator is set back to ~0 and a new flow reading is read from the rotameter 41 on line 86. The supply pressure is increased by the differential supply regulator 72 and a new flow rate is read from rotameter 41 on line 86. The process is repeated until the full differential pressure range has been examined for each back pressure desired. By varying the setting of the back pressure control valve 74 and the differential supply regulator 72 a graph like the one shown in FIG. 2 may be constructed for permeance test apparatus 70 using the flow rate measured by rotameter 41 attached to line 86 and the pressure drop across tube 18 (as measured by output pressure gauge 78 and input pressure gauge 80.) Note that the pressure drop from input pressure gauge 80 to output pressure gauge 78 affects the volumetric flow rate through the system. The mass flow rate is a function of this differential pressure and the absolute pressure in the system.

In actual operation of the permeance test apparatus 70 illustrated in FIG. 3, the back pressure control valve 74 is set at the desired operating pressure needed in line 84 for analysis by a vapor meter 88. The desired flow rate through tube 18 is maintained by the back pressure control valve 74 and the flow rate to the vapor meter may be established by adjustment of test valve 82. Using the flow rate graph constructed during a calibration process (as described in the preceding paragraph) and the pressure drop across tube 18 as measured by output pressure gauge 78 and input pressure gauge 80 the flow rate through the system can be maintained. Thereafter, as long as the absolute pressure of first fluid 14 in first fluid supply tank 12 exceeds this pre-set pressure drop across tube 18 plus the atmospheric pressure (or other "backpressure") into which first fluid 14 is discharged from permeance test apparatus 70, the combination of differential supply regulator 72 and back pressure control valve 74 will maintain a constant pressure drop across tube 18, regardless of changes in the pressure of first fluid 14 in first fluid supply tank 12, or changes in the atmospheric pressure (or other "back pressure") into which first fluid 14 is discharged from permeance test apparatus 70.

As previously mentioned, permeance test apparatus 70 includes a vapor meter 88 to measure the quantity of second fluid 28 that passes through the permeable section 24 of tube 18 and is mixed with first fluid 14 as first fluid 14 flows through tube 18 before the mixture is purged to the atmosphere via test exhaust line 90. Vapor gauge 92 is provided in vapor meter 88 for this purpose. In embodiments where first fluid 14 is a gas and second fluid 28 is water, vapor meter 88 is preferably a hygrometer that measures the dew point of the mixture of first fluid 14 and second fluid 28 that passes through vapor meter 88. Vapor meter 88 is an example of a concentration meter. A portion of the quantity of second fluid 28 that passes through the permeable section 24 of tube 18 and is mixed with first fluid 14 as first fluid 14 flows through tube 18 is exhausted through back pressure exhaust line 86. Such exhausting however, does not affect the measurement of permeance of the permeable section 24 of tube 18 because the second fluid 28 content measured in, say, parts per million by vapor meter 88, may be multiplied by the total flow rate through tube 18 (determined by a calibration curve like curve 66 in FIG. 2) to determine the total amount of second fluid 28 transported through the permeable section 24 of tube 18 over a defined period of time.

By knowing the total amount of second fluid 28 transported through the permeable section 24 of tube 18 over a defined period of time and also knowing the surface area of the permeable section 24 of tube 18, the water vapor transport parameter (WVT) defined by Equation 1 may be calculated. In a case where second fluid 28 is a vapor, its saturation vapor pressure at the test temperature ("S" in Eq'n 1) may be determined by standard, well-known means. The vapor content at "the sink" (i.e., the output concentration of the second fluid in the output mixture corresponds to "$R_2$"—the relative humidity at the vapor sink in Eq'n 2) is measured by vapor meter 88 (and converted to temperature-relative terms). The vapor content at "the source" (i.e., the concentration of second fluid 28) is typically 100% (where second fluid 28 is liquid water), or is a percentage set by a supply system such as defined in U.S. Pat. No. 6,182,951, "Method and apparatus for providing a precise amount of gas at a precise humidity," Hallman, Jr., et al. These values may be used with Equation 2 to calculate the permeance of the permeable section 24 of tube 18 to second fluid 28 in the vapor state.

When second fluid 28 is a liquid or a gas, ASTM 96 does not directly apply because liquids do not have a saturation vapor pressure. However, the gauge pressure of the fluid 28 at the location of the permeable section 24 of tube 18 may be substituted for saturation vapor pressure in Equation 2. That pressure, together with the second fluid vapor content (i.e., the output concentration of the second fluid in the output mixture) which is measured by vapor meter 88 (and converted to temperature-relative terms) may be used with Equation 2 to arrive at a non-ASTM-standard measurement of permeance of the permeable section 24 of tube 18 to second fluid 28 in the liquid or gaseous state. For purposes of a generalized description, the term "second fluid pressure" is used to encompass both (1) "saturation vapor pressure" where second fluid 28 is a vapor and (2) "gauge pressure" where second fluid 28 is a liquid or a gas.

Figure 4:
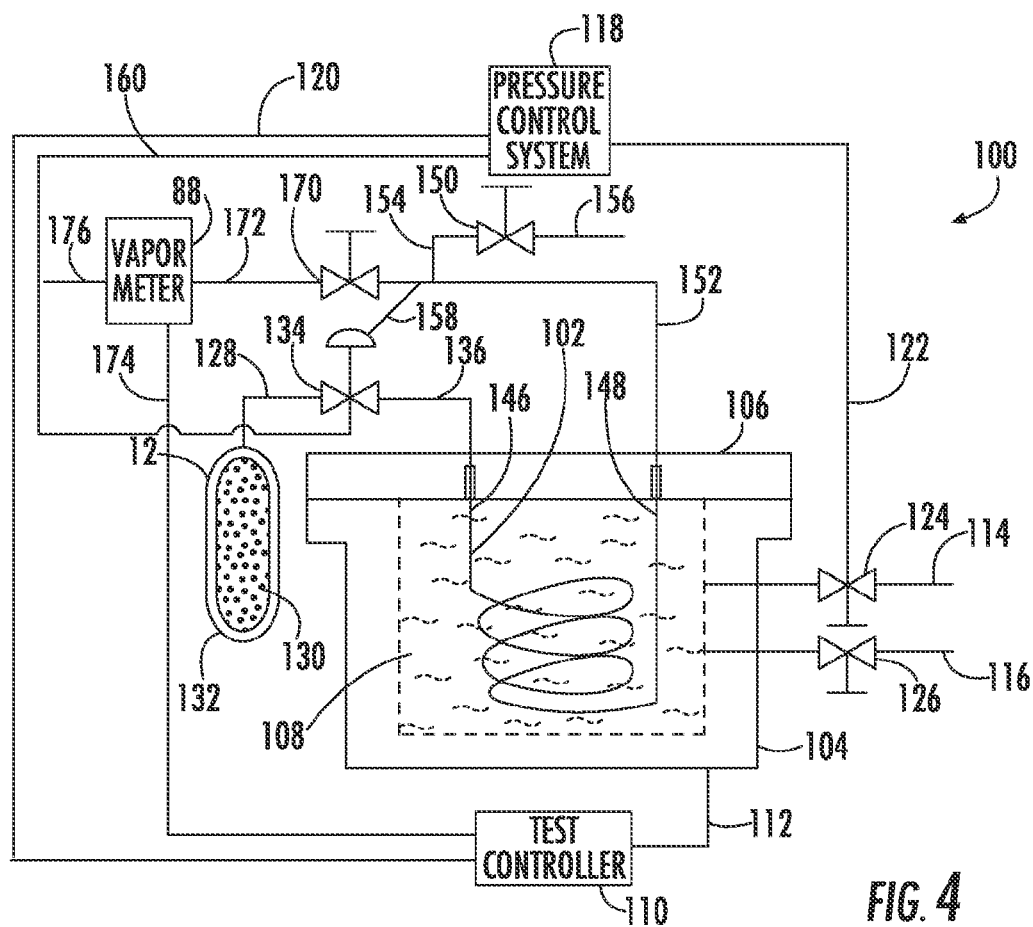
FIG. 4 is a somewhat schematic view of an alternative permeance test apparatus, including a test fixture, according to the invention.

FIG. 4 illustrates an embodiment with additional optional automation features, permeance test apparatus 100. A length of permeable tube 102 is installed as a test sample in a pressurized and controlled temperature fluid reservoir 104 through manifold 106. Permeable tube 102 is an example of a test fluid carrier. Fluid reservoir 104 contains a second fluid 108 that, for the purposes of this example is water, and at least a portion of permeable tube 102 is immersed in second fluid 108. The outside surface of permeable tube 102 that is exposed to second fluid 108 is referred to as the test area of the test sample. In cases where liquid transport through permeable tube 102 is being measured, the test area is exposed to second fluid 108 that is in the liquid phase (e.g., water). In cases where vapor transport through permeable tube 102 is being measured, the test area is exposed to second fluid 108 that is in the vapor phase (e.g., water vapor).

An optional test controller 110 is provided to automatically manage portions of the operation of permeability measurement system 100. For example, test controller 110 sets and maintains the temperature of second fluid 108 in fluid reservoir 104 using temperature control line 112. A second fluid supply line 114 is used to flow second fluid 108 into fluid reservoir 104, and second fluid return line 116 is used to remove second fluid 108 from fluid reservoir 104. In many systems second fluid supply line 114 is used to only fill fluid reservoir 104 and no subsequent fluid flow occurs. That is, the second fluid 108 is stagnant in fluid reservoir 104.

Optional pressure control system 118 is provided to set and maintain the fluid pressures in permeability measurement system 100. Pressure control system 118 is managed by test controller 110 through pressure management line 120. The operating pressure of second fluid 108 in fluid reservoir 104 is established using second fluid pressure control line 122 which sets and monitors the pressure at second fluid pressure control valve 124 in cooperation with second fluid back pressure control valve 126.

Figure 5:
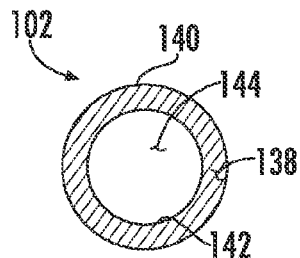
FIG. 5 is a cross-section of a permeable tube for use in the apparatus of FIG. 1, FIG. 3, or FIG. 4, according to the invention.

A first fluid source line 128 feeds a first fluid 130, such as dry nitrogen, from a tank 132 into permeable tube 102 through a differential pressure regulator 134 and first fluid supply line 136. As depicted in FIG. 5, permeable tube 102 has a wall 138 formed by an outer surface 140 and an inner surface 142. Inner surface 142 forms a hollow passageway 144 that (returning now to FIG. 4) may be used to conduct first fluid 130 from the inlet 146 of the permeable tube 102 to the outlet 148 of the permeable tube 102. First fluid supply line 136 is connected to the inlet 146 of permeable tube 102. An output mixture back pressure control valve 150 sets the pressure of first fluid 130 after it leaves permeable tube 102 through return line 152. Output mixture back pressure control valve 150 is connected to return line 152 through connector 154 and output mixture back pressure control valve 150 exhausts any overpressure output mixture to the atmosphere through output mixture back pressure exhaust line 156. Return line 152 is attached to the outlet 148 of permeable tube 102. Permeable tube 102 is an example of a test fluid carrier.

As depicted in FIG. 4, substantially all of the outer surface 140 (FIG. 5) of permeable tube 102 is in contact with second fluid 108, and consequently the outer surface 140 of permeable tube 102 constitutes the test area of permeable tube 102. The inner surface 142 (FIG. 5) of permeable tube 102 comprises the surface area opposed to the test area of permeable tube 102. The flowing of first fluid 130 through the hollow passageway 144 (FIG. 5) of permeable tube 102 is an example of flowing a fluid over a surface area (142) opposed to the test area (140) of a test sample.

A pilot tube 158 is attached between return line 152 (near output mixture back pressure control valve 150) and differential pressure regulator 134, thereby maintaining a constant pressure drop through permeable tube 102. Pressure control system 118, operating under the automated supervision of test controller 110 through pressure management line 118, uses first fluid pressure control line 160 to set the pressure drop through first fluid supply line 136, permeable tube 102, and return line 152 to output mixture back pressure control valve 150.

In actual test operations, a portion of second fluid 108 in fluid reservoir 104 permeates permeable tube 102 through its test area. That is, a quantity of second fluid 108 flows through the wall 138 of permeable tube 102 into the hollow passageway 144 of permeable tube 102. That quantity of second fluid 108 that flows into the hollow passageway 144 is entrained in first fluid 130 flowing through the hollow passageway 144 of permeable tube 102.

Figure 6:
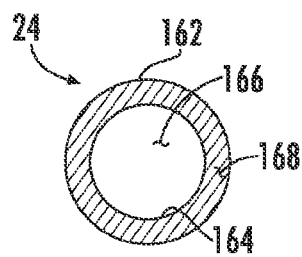
FIG. 6 is a cross-section of a permeable tube for use in the apparatus of FIG. 1, FIG. 3, or FIG. 4, according to the invention.

In some embodiments as previously depicted in FIGS. 1 and 3, a tube 18 is configured so that only a portion (permeable section 24) of the length of the tube 18 is permeable. In some embodiments the entire tube 18 consists of permeable section 24. For testing, the permeable section 24, or at least a part of it, is immersed in second fluid 28. Referring to FIG. 6, the outside surface 162 of the permeable section 24 of tube 18 (FIG. 3) that is immersed in second fluid 28 (FIG. 3) in second fluid reservoir 26 (FIG. 3) is called the test area of the test sample. The permeable section 24 has an inner surface 164 that forms a hollow passageway 166. Hollow passageway 166 provides the same function as hollow passageway 144 previously described for permeable tube 102. Since the wall 168 of the permeable section 24 of tube 18 has a finite thickness, at any point in time a quantity of second fluid 108 is resident in the wall 168 of the permeable section 24 of tube 18. In the context of a tubular test fluid carrier, a reference to a fluid that permeates the test fluid carrier is a reference to a fluid (e.g., second fluid 108 in FIG. 4) that has passed through the wall (e.g., wall 168 of permeable section 24 of tube 18 in FIG. 6) of a tube that is immersed in a second fluid (e.g., second fluid 108 in FIG. 4) and flows into the hollow passageway (e.g., hollow passageway 166) of the test fluid carrier. This fluid is also referred to as fluid that has permeated "through the test sample."

If a gas at a fixed pressure is applied to the entrance of a long tube and the output pressure is fixed, such as at atmospheric pressure, then the flow rate of the gas through the tube is simply a function of the pressure drop across the tube. Quantitatively, the flow rate, $Q_V$, is equal to $\Delta P/R_F$, where $\Delta P$ is the pressure drop and $R_F$ is the fluid resistance in the tube. $R_F$ is a function of the cross-sectional area of the tube, the tube's length, and the viscosity of the fluid, all of which are substantially constant for a particular geometry. Referring again to FIG. 4, in the most preferred embodiments, the geometry of first fluid supply line 136, permeable tube 102, and return line 152 are fixed. Therefore, the volumetric flow rate of first fluid 130 (and second fluid 108 that permeates through permeable tube 102) that flows out return line 152 may be calculated from and controlled by the pressure drop (through first fluid supply line 136, permeable tube 102, and return line 152 to output mixture back pressure control valve 150) that is established by differential pressure regulator 134. It should be noted that this is the essence of most embodiments of the system. The flow determination and control by pressure drop may be done after the flow rate has been measured and correlated to a pressure drop for a specific system configuration, i.e., a fixed resistance. Pressure drop and flow rate are directly related and knowing how a change in one affects the other allows for the desired control to be achieved. By knowing this relationship between pressure drop and flow rate, it is possible to control and adjust the flow rate better than it can be measured directly. In other words, once the relationship between flow rate and pressure drop is known (as illustrated in by graph 60 in FIG. 2) adjustments to the pressure have a higher precision (typically on the order of a few parts per thousand) than the precision achievable by direct flow measurement (e.g., a rotameter) which is typically no better than a few parts per hundred.

Continuing with FIG. 4, the quantity of first fluid 130 that flows into permeable tube 102 and the quantity of second fluid 108 that permeated into the hollow passageway 144 of permeable tube 102 are transported via test control valve 170 and output mixture test line 172 into vapor meter 88. Vapor meter 88 measures the amount of second fluid 108 (that was originally vapor or has become vapor) that is entrained per unit of volume of first fluid 130 and second fluid 108 and flows through output mixture test line 172. This information is passed to test controller 110 (using vapor meter data line 174) where the permeance of permeable tube 102 is calculated by using the rate at which second fluid 108 has been determined to pass through the test area of permeable tube 102 at the pressure differential level set between second fluid pressure control valve 124 (in cooperation with second fluid back pressure control valve 126) and differential pressure regulator 134 (in cooperation with output mixture back pressure control valve 150). The tested output mixture exits the vapor meter 88 of permeance test apparatus 100 through test mixture exhaust line 176. An untested (but compositionally equivalent) portion of the output mixture leaves permeance test apparatus 100 through back pressure exhaust line 156 from the output mixture back pressure control valve 150.

Figure 7:
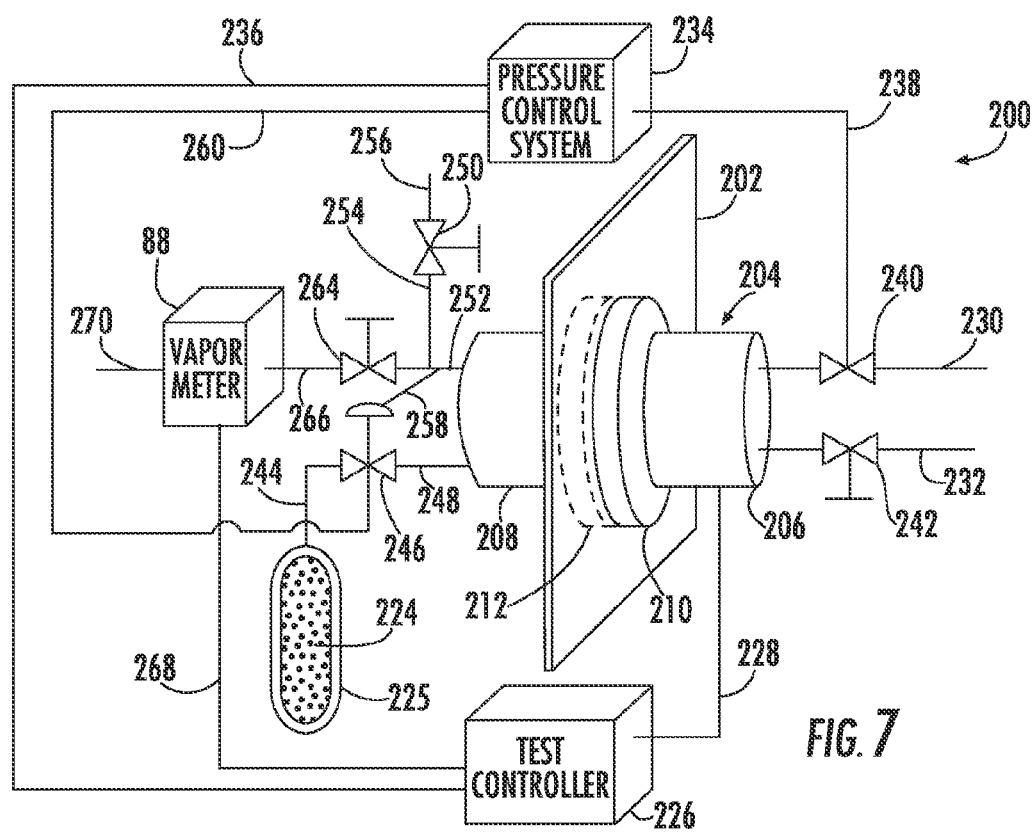
FIG. 7 is a somewhat schematic view of an alternative permeance test apparatus, including a test fixture, according to the invention.

FIG. 7 illustrates an embodiment of a permeance measurement system 200. A material test sheet 202 is loaded into a fixture 204 that comprises a controlled pressure and temperature second fluid reservoir 206 and a first fluid compartment 208. Material test sheet 202 is shown mounted between a first flange 210 on second fluid reservoir 206 and a second flange 212 on first fluid compartment 208. In some embodiments the fixture 204 may further comprise a test sample carrier, a mounting slide, or other similar device to position material test sheet 202 between second fluid reservoir 206 and first fluid compartment 208.

A second fluid supply line 230 flows a second fluid 218 (shown in FIG. 8), typically water, into second fluid reservoir 206, and a second fluid return line 232 is provided to remove second fluid 218 from second fluid reservoir 206.

A first fluid supply line 244 provides a flow of first fluid 224, for example dry nitrogen, from first fluid supply tank 225 to first fluid compartment 208, through differential pressure regulator 246 and first fluid source line 248. An output mixture back pressure control valve 250 establishes the pressure leaving first fluid compartment 208 through a first fluid return line 252. Output mixture back pressure control valve 250 is connected to the first fluid return line 252 through connector 254 and output mixture back pressure control valve 250 exhausts any overpressure output mixture to the atmosphere through output mixture back pressure exhaust line 256.

Pilot tube 258 in FIG. 7 feeds the pressure in first fluid return line 252, at a point adjacent to back pressure control valve 250, into differential pressure regulator 246 thereby maintaining a constant pressure drop from differential pressure regulator 246 through first fluid source line 248, first fluid compartment 208, first fluid return line 252 to back pressure control valve 250. Optional pressure control system 234, operating under the automated supervision of optional test controller 226 through pressure management line 236, uses first fluid pressure control line 260 to set the pressure drop through first fluid source line 248, first fluid compartment 208, and first fluid return line 252 to back pressure control valve 250.

As with permeance test apparatus 100 depicted in FIG. 4, it is necessary to calibrate permeance test apparatus 200 in FIG. 7 to create a pressure/flow rate curve of the type illustrated as graph 60 in FIG. 2. In the most preferred embodiments, the physical geometry of first fluid source line 248, first fluid compartment 208, and first fluid return line 252 is fixed. Consequently the "resistance" of first fluid source line 248, first fluid compartment 208, and first fluid return line 252 is fixed. Because the resistance is fixed, the volumetric flow rate through first fluid source line 248, first fluid compartment 208, and first fluid return line 252 may be expressed solely as a function of the pressure drop across those elements. Generally if flow is laminar the flow rate is a linear function of pressure drop; if flow is turbulent the flow rate is an exponential function of the pressure drop that is established by differential pressure regulator 246. In some cases it may be necessary to artificially increase the length and/or shrink the diameter of first fluid source line 248 and/or first fluid return line 252 in order to generate a pressure/flow rate curve that is steep enough to provide adequate resolution of flow rate readings based on pressure differentials. The mass flow rate of a gas/vapor output mixture flowing out first fluid return line 252 may be determined by various techniques such as (1) using a hygrometer for moisture, (2) using an IR gas analyzer (for some gases), or (3) calculating the mass flow rate using the density of the output mixture and the partial pressures of the gas/vapor components. Alternately, the mass flow rate may be determined simply by measuring the volumetric flow rate by such devices as a rotameter or mass flow meter and calculating the mass flow rate using the molecular weights of the constituent fluids.

As illustrated in FIG. 7, some embodiments incorporate an optional test controller 226 to provide automated control of the overall operation of permeance test apparatus 200. For example, optional test controller 226 uses temperature control line 228 to establish and monitor the temperature of controlled pressure and temperature second fluid reservoir 206. Some embodiments also include an optional pressure control system 234 which, under the automated supervision of test controller 226 through pressure management line 236, controls the pressures in second fluid reservoir 206 and first fluid compartment 208. Pressure management line 236 is an electronic control circuit, a pneumatic or hydraulic line, or similar linkage that includes both pressure controlling and reporting mechanisms. Optional pressure control system 234 controls the pressure in second fluid reservoir 206 by using pressure control line 238 (which is also an electronic control circuit, a pneumatic or hydraulic line, or similar linkage) to control second fluid pressure control valve 240. Fluid pressure control valve is an electronically controlled valve. Typically second fluid flow control valve 242 is manually set to a fixed flow rate and second fluid pressure control valve 240 works in cooperation with second fluid flow control valve 242 to set the pressure in second fluid reservoir 206.

Figure 8:
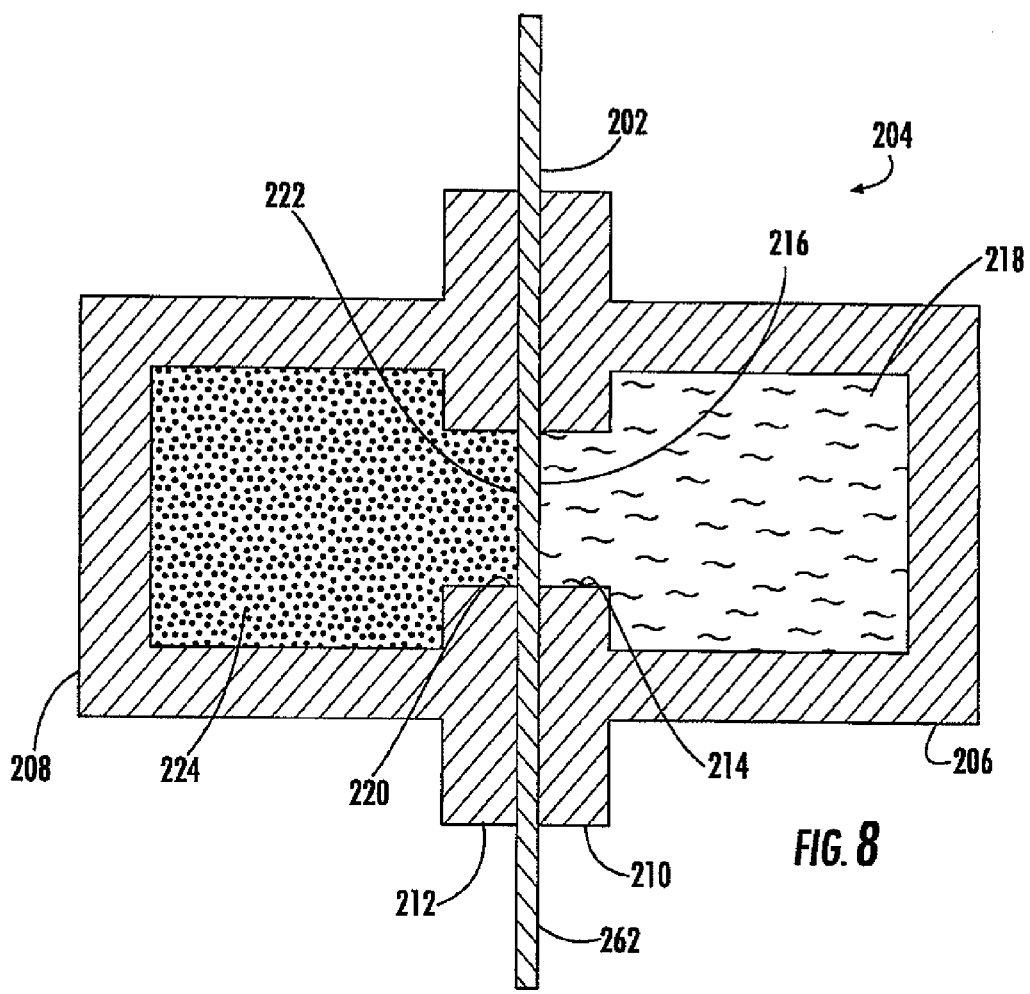
FIG. 8 is cross-section view of a test fixture according to the invention.

FIG. 8 illustrates further details of fixture 204. An opening 214 in flange 210 exposes a test area 216 in material test sheet 202 to second fluid 218 in second fluid reservoir 206. A geometrically matching opening 220 in second flange 212 exposes a surface area (e.g., 222) opposed to the test area (e.g., 216) of material test sheet 202 to first fluid 224 in first fluid compartment 208. The flowing of first fluid 224 through first fluid compartment 208 where it contacts surface area 222 of material test sheet 202 that is opposed to the test area 216 of material test sheet 202 that is contacted by second fluid 218 is an example of "flowing a fluid (e.g., 224) over the surface area (e.g., 222) opposed to a test area (e.g., 216) of a test sample (e.g., 202)."

In operation, a portion of second fluid 218 (which may be liquid, gas, or vapor) permeates through the test area 216 of material test sheet 202 and enters first fluid compartment 208. First fluid compartment 208 represents a collection chamber for the permeate and gas output mixture. Since the wall 262 (FIG. 8) of material test sheet 202 has a finite thickness, at any point in time a quantity of second fluid 218 is resident in the wall 262 of material test sheet 202 between the test area 216 and the surface area (e.g., 222) opposed to the test area (e.g., 216). A reference to "fluid that permeates through the test area" is, in the embodiment of FIGS. 7 and 8, a reference to a fluid (e.g., second fluid 218) that has passed through the wall 262 of material test sheet 202 at test area 216 into first fluid compartment 208. That is, the quantity of second fluid 218 that is resident in the wall 262 of material test sheet 202 is not counted as fluid that has permeated "through the test area of the test sample."

Referring now to FIGS. 7 and 8, the volume of first fluid 224 plus the volume of second fluid 218 that has permeated through material test sheet 202 flows out test control valve 264 through mixture test line 266 into vapor meter 88. Vapor meter 88 measures the amount of second fluid 218 (moisture, in the case where second fluid 218 is water) that is entrained as vapor per unit of volume of first fluid 224 and second fluid 218 flowing through the vapor meter 88. This information is passed to test controller 226 (using vapor meter data line 268) where the permeance of material test sheet 202 is calculated using the rate at which second fluid 218 has been determined to have permeated through the test area 216 of material test sheet 202 at the pressure differential level set between second fluid pressure control valve 240 and differential pressure regulator 246. A portion of the output mixture of second fluid 218 and first fluid 224 exits the permeance test apparatus 200 through test mixture exhaust line 270 and the excess flow exits via output mixture back pressure exhaust line 256. If test control valve 264 is closed the total flow rate is constant and maintained and exhausted through back pressure exhaust line 256.

The permeance of a material is dependent upon, among several factors, the material being permeated and the temperature of the fluid vapor that permeates the material. In the most preferred embodiments, the test controller (110, in FIG. 4, 226 in FIG. 7) is programmed to vary the temperature of the second fluid (108 in FIG. 4, 218 in FIG. 8) in a variable temperature reservoir (second fluid reservoir 104 in FIG. 4, second fluid reservoir 206 in FIG. 7) and measure the difference in permeance of a test sample (e.g., permeable tube 102 in FIG. 4, material test sheet 202 in FIG. 7) over the different temperatures.

The permeance of most materials is also dependent upon the pressure differential across the material. Consequently, in the most preferred embodiments the test controller (110 in FIG. 4, 226 in FIG. 7) is programmed to vary the pressures set by liquid pressure control valve (124 in FIG. 4, 240 in FIG. 7) and/or differential pressure regulator (134 in FIG. 4, 246 in FIG. 7), and measure the permeance of the test sample (e.g., permeable tube 102 in FIG. 4, material test sheet 202 in FIG. 7) over different pressure differentials, including different saturation vapor pressures. A test controller that is configured to adjust pressures in this manner is an example of a pressure differential apparatus.

Many materials, especially polymeric materials, also exhibit a different permeance depending upon their strain profile. The term strain profile refers to a deformation of the material under stress, compared to its shape without stress. Typically such deformation is measured in terms of percent elongation. The percent elongation may include deformation either within or beyond the elastic region of the material. The strain profile of a material test sample may be modified by stressing it in one or in more than one axis. In some embodiments, different strain profiles may be induced by controlling the differential pressure across the material test sample. In other embodiments, the test fixture that mounts the material test sample may include mechanisms to mechanically induce different strain profiles in the material test sample. In embodiments employing a system for inducing strain in a material test sample the permeance of a material test sample is typically measured several times at different strain profiles.

In many applications it is important to measure the permeance of a material under a specified supply condition for the fluid that permeates through a material test sheet. For example, it is often desired to test the permeance in an environment where the fluid supply is a vapor instead of a liquid. To accommodate this objective, many embodiments use a vapor as the second fluid (108 in FIG. 4, 218 in FIG. 8) in a permeance test apparatus (100 in FIG. 4, 200 in FIG. 7). In some instances the vapor is a pure chemical, such as 100% steam. In other instances a second fluid comprising a concentration (mass ratio) of a first constituent in a combination with a second constituent, such as water vapor and nitrogen, is desired. For example, it may be desired to test the permeance of a material test sample (e.g., permeable tube 102 in FIG. 4 or material test sheet 202 in FIG. 7) at a concentration of 20% water vapor and 80% dry air. In these embodiments it is very beneficial to provide a well-controlled mixture of water vapor and air that is flowed into a fluid reservoir (e.g., second fluid reservoir 104 in FIG. 4, second fluid reservoir 206 in FIG. 7). The apparatus of U.S. Pat. No. 6,182,951—"Method and apparatus for providing a precise amount of gas at a precise humidity," Hallman, Jr., et al., may be used as a mixer for varying the concentration of the vapor in the "liquid bath." Other devices that may be used as a mixer for varying the concentration of the mixture in the embodiments of FIG. 4, FIG. 7, and in other embodiments, include a humidity test chamber or an environmental chamber that is used as the "liquid bath." When the chemical composition of the liquid is varied, the concentration of the components of the composition may be varied by mixers comprising an automated or manual chemical dispensing device, a metered flow mixer, or a manually measured and mixed batch makeup system.

In some applications the second fluid (e.g., second fluid 108 in the embodiment of FIG. 4, or second fluid 218 in the embodiment of FIG. 8) comprises a liquid mixture, such as alcohol in water. In such applications it is useful to vary the concentration of the liquid mixture, and conduct the permeance test at different concentrations. This may be accomplished by using standard laboratory chemical dilution/dispensing apparatuses to provide the second fluid to the permeance test apparatus through the second fluid supply line (e.g., element 114 in FIG. 4 or element 230 in FIG. 7).

FIG. 9 illustrates a method embodiment for measuring the permeance of a test material to a second fluid at a specific source concentration level and under specific temperature and pressure conditions. Method 300 begins with step 302 in which the correlation between flow rate and pressure drop for a first fluid is established in a test apparatus. The method continues in step 304 by establishing a source concentration of a second fluid. Typically the second fluid is water. In some applications liquid water is used, and in some applications water vapor is used. When pure liquid water is used, the source concentration that is established intrinsically is one hundred percent. When water vapor is used, the source concentration may vary from trace amounts (e.g. parts per million) to one hundred percent.

In step 306 the second fluid is provided to the process in a fluid reservoir at a first temperature. Typically where water is the second fluid, the reservoir is a water bath, a humidity chamber, or an environmental chamber.

A test area of a test sample at a first strain profile is exposed to the second fluid in the reservoir according to step 308. In step 310 a flow of the first fluid at a first pressure differential is directed over the surface area of the test sample that is opposed to the test area that was exposed to the second fluid in step 308. The first fluid is typically a dry gas. When the test sample is a sheet material, the sheet material is typically mounted in a fixture in which both sides of an area of the material to be tested are exposed to a treatment environment. One side of the sheet (the test area) is exposed to the second fluid and the other side of the sheet (equal in size to and opposed to the test area) is exposed to the first fluid. When the test sample is a tube, the outside surface of a portion of the tube (the test area) is typically exposed to the second fluid and the inside of the tube (opposite the test area) is exposed to the first fluid. In this step, unless the test sample is totally impermeable to the first fluid, the laws of physics dictate that some amount of the first fluid permeates (goes through) the test area of the test material.

In step 312 the amount of second fluid that permeates the test area of the test material is combined with the first fluid that flows over the surface opposed to the test area of the test sample to create an output mixture. When water is the second fluid and dry air is the first fluid, the output mixture will be air with specific moisture content.

Step 314 measures the mass flow rate of the first fluid and the mass flow rate of the second fluid in the output mixture. Typically, the geometry of the apparatus is defined and maintained in a configuration such that the mass flow rate of the mixture is determined by measuring the pressure drop from where the first fluid flow is started to where the output mixture is collected, and measuring the output concentration of the second fluid in the output mixture. (Note that the correlation of flow rate to pressure drop has been made prior to step 314, as step 302.) When the second fluid is liquid water (or water vapor) and the first fluid is dry air, the measurement of the output concentration of the first fluid in the output mixture may be made using a hygrometer.

In step 316 the permeance of the test sample material is calculated. This step entails measurement of the concentration differential across the test area of the test sample, i.e., the difference between the source concentration of the second fluid in the second fluid reservoir and the output concentration of the second fluid in the output mixture collection system. The permeance of the test sample is the mass flow rate of the second fluid divided by the product of (1) the difference in vapor concentration across the test area, and (2) the test area, and (3) time. The permeability of the test material is the permeance multiplied by the thickness of the test material in the test area. In the case where the second fluid is water vapor, the output concentration of water vapor is preferably determined by a General Eastern dew point/frost point hygrometer, or equivalent device.

Method 300 includes four optional steps, 318, 320, 322, and 324. In optional step 318 the pressure differential across the test sample is modified from the previous setting(s) and steps 312, 314 and 316 are repeated for each different pressure differential, as illustrated by process loop 326. In optional step 320, the strain profile of the material test sample is modified (this strain can be induced by a pressure differential or a deflection of the sample holder resulting in a strain of the sample), and steps 310-316 are repeated for each different strain profile, as illustrated by process loop 328. In optional step 322, the temperature of the first fluid is changed from the previous setting(s) and steps 308 through 316 are repeated for each different temperature, as illustrated by optional loop 330. In optional step 324, the source concentration of the second fluid is varied from the initial source concentration and steps 306 through 316 are repeated for each different source concentration, as illustrated by process loop 332. The variation in source concentration may be a variation in physical composition (such as percent humidity) or a variation in chemical composition (such as percent alcohol in water).

The foregoing description of preferred embodiments for this invention has been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A system for determining a permeance of a material, the system comprising:
- a material test sheet having a first surface and an opposing second surface;
- a collection chamber having a first fluid source line;
- a first fluid source for continuously flowing a first fluid at a first pressure into the collection chamber through the first fluid source line;
- a fluid reservoir containing a second fluid;
- a fixture for disposing the material test sheet between the fluid reservoir and the collection chamber wherein (a) a test area of the first surface of the material test sheet is exposed to the second fluid and (b) the area on the second surface of the material test sheet that opposes the test area of the first surface is exposed to the first fluid in the collection chamber, whereby a portion of the second fluid permeates through the test area into the collection chamber to form in the collection chamber an output mixture of the permeated second fluid and the first fluid at a concentration level;
- a collection removal line for removing substantially all of the output mixture; and
- a pressure gauge in pressure communication with the collection removal line, for measuring a second pressure of the output mixture in the collection removal line; and
- a concentration meter configured to measure the concentration level of the second fluid in the output mixture exiting from the collection chamber through the collection removal line, wherein the permeance of the material is determined using the first pressure, the second pressure, and the concentration level of the second fluid in the output mixture.

2. The system of claim 1 further comprising a flowmeter configured to measure a flow rate of the first fluid and the second fluid through the collection removal line.

3. The system of claim 1 further comprising:
- a back pressure control valve configured to set the second pressure of the mixture of the first fluid and the second fluid at the collection removal line; and
- a differential pressure regulator in pressure communication with the mixture of the first fluid and the second fluid at the collection removal line and configured to set the first pressure of the first fluid in the first fluid source line at a pressure level that maintains a constant pressure differential between the first pressure and the second pressure.

4. The system of claim 1 wherein the fluid reservoir comprises a variable temperature reservoir for varying the temperature of the second fluid.

* * * * *